(12) United States Patent
Kurfürst et al.

(10) Patent No.: US 8,440,445 B2
(45) Date of Patent: May 14, 2013

(54) NEUTRAL PROTEASE (NP) AND PRODUCT BY USING NEUTRAL PROTEASE FOR TISSUE DISSOCIATION AS WELL AS METHOD FOR THE PRODUCTION THEREOF

(75) Inventors: Manfred Kurfürst, Moorrege (DE); Christian Raemsch, Uetersen (DE); Nicole Raemsch-Guenther, Uetersen (DE); Olaf Friedrich, Tornesch (DE); Silke Huettler, Uetersen (DE); Daniel Brandhorst, Linden (DE); Thierry Berney, Arenthon (FR); Pascal Bucher, Geneva (CH); Heide Brandhorst, Linden (DE)

(73) Assignee: Nordmark Arzneimittel GmbH & Co. KG, Uetersen (DE)

( * ) Notice: Subject to any disclaimer, the term of this patent is extended or adjusted under 35 U.S.C. 154(b) by 0 days.

(21) Appl. No.: 10/869,313

(22) Filed: Jun. 16, 2004

(65) Prior Publication Data
US 2005/0142632 A1    Jun. 30, 2005

(30) Foreign Application Priority Data

Jul. 9, 2003 (DE) ................... 103 31 171

(51) Int. Cl.
*C12N 9/52* (2006.01)

(52) U.S. Cl.
USPC .......... 435/220; 435/68.1; 435/219; 435/366; 435/378; 435/380; 435/381

(58) Field of Classification Search .............. 435/68.1, 435/219, 220
See application file for complete search history.

(56) References Cited

U.S. PATENT DOCUMENTS

| 5,853,976 | A | | 12/1998 | Hesse et al. | |
| 5,952,215 | A | * | 9/1999 | Dwulet et al. | 435/220 |
| 5,989,888 | A | * | 11/1999 | Dwulet et al. | 435/220 |
| 2004/0137596 | A1 | | 7/2004 | Kurfürst et al. | |

FOREIGN PATENT DOCUMENTS

| JP | 7-313159 | 12/1995 |
| WO | WO 96/19583 | 6/1996 |
| WO | WO 03/004628 A2 | 1/2003 |

OTHER PUBLICATIONS

Wolters, GHJ et al. An analysis of the role of collagenase and protease in the enzymatic dissociation of the rat pancreas for islet isolation. Diabetologia. 1992. 35: 735-742.*
Hefley, TJ et al. Enzymatic isolation of cells from neonatal calvaria using two purified enzymes from *Clostridium histolyticum*. Experimental Cell Research. 1983. 149: 227-236.*
Ricordi, C et al. Improved human islet isolation outcome from marginal donors following addition of oxygenated perfluorocarbon to the cold-storage solution. Transplantation. May 15, 2003. 75(9): 1524-1527.*
Japanese Office Action issued Aug. 12, 2008, in Patent Application No. 2004-181373 (partial English-language translation only).
Japanese Office Action issued May 11, 2010, in Patent Application No. 2010-005801 (partial English-language translation only).
European Search Report issued Aug. 25, 2005, in Patent Application No. 04012321.8 (with English-language translation).
Shinichi Matsumoto, et al., "Effect of the Two-Layer (University of Wisconsin Solution-Perfluorochemical Plus $O_2$) Method of Pancreas Preservation on Human Islet Isolation, As Assessed by the Edmonton Isolation Protocol[1]", Transplantation, vol. 74, No. 10, Nov. 27, 2002, pp. 1414-1419.

* cited by examiner

*Primary Examiner* — Allison Ford
*Assistant Examiner* — Susan E Fernandez
(74) *Attorney, Agent, or Firm* — Oblon, Spivak, McClelland, Maier & Neustadt, L.L.P.

(57) ABSTRACT

The use of a neutral protease (NP) together with a collagenase consists in that a neutral protease which is not contained in a collagenase enzyme preparation and which is not produced by a recombinant production ia mixed before the beginning of a tissue dissociation with a collagenase or a collagenase enzyme preparation with an individual dosage of the quantitative proportions of neutral protease and collagenase for improving the isolation results with respect to yield, viability and integrity of the cells.

2 Claims, No Drawings

NEUTRAL PROTEASE (NP) AND PRODUCT BY USING NEUTRAL PROTEASE FOR TISSUE DISSOCIATION AS WELL AS METHOD FOR THE PRODUCTION THEREOF

FIELD OF APPLICATION

This invention relates to the use of a neutral protease (NP) for a tissue dissociation.

PRIOR ART

The DE 44 45 891 A1 describes a recombinant protease (neutral protease, NP) from *Clostridium histolyticum* and its use for the insolation of cells and cell aggregates. This being, it is started from the fact that, in order to use natural protease for the isolation of cells and cell aggregates at a greater extent, it is necessary to make available the neutral protease in reproducible quality and in big quantities, what is possible due to a recombinant method of production. However, the cloning of the neutral protease is not possible right away since hardly sequences of *Clostridium histolyticum* are known (clostripain, two collagenases as well as one ribosomal RNA sequence). Thus, conclusions to the Codon usage and thus the restriction of the degeneracy of usable oligonucleotides is not possible. Therefore, the DNA sequence of the neutral protease from *Clostridium histolyticum* as well as its recombinant production should be made available, namely by a DNA sequence which codes for a proteine with the activity of the neutral protease from *Clostridium histolyticum*, whereby the DNA sequence is selected from the group a.) of the DNA sequence shown in SEQ ID NO: 1 or a DNA sequence complementary hereto,
b.) nucleic acid sequences which hybridize with the sequence shown in SEQ ID NO,
c.) nucleic acid sequences which would hybridize with one of the sequences mentioned in a.) and b.) without the degeneracy of the genetic code.

The method for the dissolution of cell tissue and release of cells or cell aggregates contained therein is characterized by incubation of the cell tissue with a recombinant neutral protease from *Clostridium histolyticum* which is made of SEQ ID NO:1 or a sequence which is coded within the scope of the degeneracy of the genetic code for the same amino acid sequence and is the product of a prokaryontic or eukaryontic expression of an exogenous DNA up to the release of the cells or cell aggregates in the desired extent and separation of the cells or cell agregates from the cell tissue parts. The use of the enzyme thus obtained is not demonstrated.

A ready-made product, produced by the manufacturer from a mixture of certain ratios of collagenases I and II and neutral protease can be seen in U.S. Pat. No. 5,989,888.

According to this method, a neutral protease which is contained in a collagenase preparation is used so that a high stability of the enzymes is not achieved. Add to this that, when the neutral protease is contained for a longer time in the collagenase, a reduction of the enzyme activity appears with moisture.

SUMMARY OF THE INVENTION

The aim of this invention is to make available a product, a method for its production as well as its use for a tissue dissociation with which improved isolation results are achieved with respect to yield, viability and integrity of the cells.

This aim is achieved by a product with the characteristics of claim 1 with a method according to claim 3 and with an use according to claim 9.

The product according to the invention consists of a separate A component from a protease (NP) from *Clostridium histolyticum* which is not contained in a collagenase enzyme preparation and of a separate B component from collagenase or from a collagenase enzyme preparation, whereby for a tissue dissociation the A component is added to the B component in respectively necessary quantities before the beginning of the dissociation.

The neutral protease used is not made available by a recombinant production.

The method according to the invention consists in that a separate A component from a neutral protease (NP) from *Clostridium histolyticum* with a defined content which is not contained in a collagenase enzyme preparation and which is not produced by a recombinant production is mixed to a separate B component from a purified or partially purified collagenase or from a collagenase enzyme preparation with an individual dosage of the quantitative ratios of both components before the beginning of the tissue dissociation.

The use according to the invention consists in a completely purified neutral protease (NP) not contained in a collagenase enzyme preparation in a respectively selected quantity as an individual admixture to a collagenase or a collagenase enzyme preparation for the tissue dissociation or the isolation of cells or multicellular aggregates, for example made of tissues, for improving the isolation results with respect to yield, viability and integrity of the cells.

The use of neutral protease together with purified or partially purified collagenase with a defined content of neutral protease with an individual dosage of the quantitative ratios of both components is particularly advantageous, whereby neutral protease is used which is not produced by a recombinant production.

Because of the product according to the invention and of the use according to the invention of neutral protease for a tissue dissociation, an improvement of the isolation results with respect to yield, viability and integrity of the cells is achieved in that neutral protease (NP) of *Clostridium histolyticum* is used separately, not contained in a collagenase enzyme preparation, by an individual adding of the neutral protease to a collagenase enzyme preparation or of collagenase or of collagenase I and II for the isolation of cells or cell aggregates of tissues. Neutral protease of *Clostridium histolyticum* is used. This being, individuality depending on the tissue type and/or condition prevails. The procedure is such that the adding of collagenase and neutral protease takes place respectively depending on the quantity of tissue. The neutral protease is not contained in a collagenase preparation so that a higher stability of the enzymes is achieved. Add to this that no mixture of neutral protease and collagenase produced by a producer and kept in store or in stock is used. Neutral protease and collagenase are combined shortly before the beginning of a tissue dissociation.

The demonstration of the function by digestion depending on species, condition of the organ and position of the organ is particularly advantageous. Surprisingly, it has shown that solely due to the variation of the addition of neutral protease, the isolation results could be significantly improved with respect to the yield of islet cell equivalents, viability, integrity of the islet cells or islet cell aggregates. This being, the adding of collagenase plays a less critical part since it is an enzyme which is relatively little toxic for the cells. The quantity of neutral protease is more critical since the enzyme has a cell deteriorating action in too big quantities, in too low quantities the tissue dissociation remains uncomplete, thus the yield of isolated islet cells and islet cell aggregates is lower. In order to be able to dose individually the neutral protease, it is important as well that a purified or partially purified collagenase is used which contains low quantities of other proteolytic activities such as that of the neutral protease.

Advantageous configurations of the invention are the subject of the subclaims.

DESCRIPTION OF THE PREFERRED EMBODIMENTS

Optimization of the islet isolation from porcine and human pancreas by donor related enzyme adaptation.

The isolation of the islets of Langerhans from the pancreatic tissue takes up a special position in the field of the enzymatic cell separation. Contrary to the isolation of other cell types from different tissues, the islet isolation is characterized by the attempt to separate a multicellular cell aggregate, the islet, from another organ, the pancreas, by preserving the morphologic integrity. This aim makes special demands on the methodology applied.

The semi-automatic digestion filtration method has become established as a standard procedure for the isolation of islets from the pancreas of bigger animals, this method combining an enzymatic digestion with a mechanical dissociation of the pancreas (1). The selection of appropriate collagenolytic enzymes or protease mixtures constitutes a special challenge. These mixtures should, in the ideal case, guarantee a maximal dissociation of the exocrine tissue for a minimal dissociation of the islet tissue. Among the multitude of the enzymes existing in impure collagenolytic protease mixtures, collagenases of the class I and class II have been identified as being essential for the islet release from the pancreas of rats (2, 3) and pigs (4). Since pure collagenases only lead to an insufficient digestion of the pancreas tissue of dog (5) and rat (2), further proteases in form of dispase (6), neutral protease (2) or trypsin (4) seem to be necessary for an efficient release of islets. Own preliminary findings on porcine pancreas also speak for a positively synergitic effect of unspecific "neutral protease" onto the islet release. The acting mechanism of unspecific proteases is possibly the release of collagen fibres due to the proteolytic degradation of proteoglycans so that collagenolytic activities obtain an easier access to their substrates. Furthermore, a stronger hydrolysis of collagen fragments through unspecific protease is discussed (2). An excess of neutral protease can accelerate the proteolytic degradation of collagenase itself though and contribute to the islet disintegration, because of the lysis of protease sensitive adhesion molecules (cell adhesion molecules CAM). On the other hand, it could be shown on rats that islets seem to be relatively resistant to the proteolytic action of pure collagenase (2).

When evaluating the quoted examinations, it must be taken into consideration that the sensitivity of islets to the destructive effect of neutral proteases depends on the species and is determined by the morphological partition pattern of the cell contacts and of the specific character of the collagen matrix (8, 9). So, for the pig, the peninsular collagen content is the lowest among all the species examined until now (dog, human, rat, cow) and the specific character of a protective connective tissue capsule only exists rudimentally (10-12). On the other hand, in this species, the highest number of cell contacts between endocrine and exocrine pancreatic cells is to be found (8). Thus, the requirements which are made to a collagenolytic protease mixture with respect to the activity profile, depends on the donor species which is used. These important findings lead to the development and commercial utilization of enzyme mixtures for the isolation of islets from the pancreas of the rat (Liberase RI©), of the dog (Liberase C©), of the pig (Liberase PI©) and of the human being ((Liberase HI©) by the Roche company. These products differ essentially in the content of neutral protease.

Besides species depending differences, there are naturally also intraspecific and individual donor variabilities. For the human pancreas donor, above all an age dependent character of factors such as nutritional condition, consumer habits and prior affections induces an enormous variation of the yield after isolation of the islets. As for the pig, above all the donors' age is to be indicated as a highly significant variable for an isolable islet mass, what lets appear that young donors <25 years are in many cases unsuitable for a successful islet isolation (13-15). Age-related changes, such as an increased body mass index (16) which is often associated with a pancreatic fibrillization (17, 18) or a pancreas fatty degeneration (19) increase the isolation ability of islets from the human pancreas. Although these morphological changes let appear even the pancreas of geriatric donors as suitable for the isolation of islets (20), an age-related reduction of the islets functionality is also to be taken into consideration (15, 21, 22). Thus, just an extension of the donors pool with juvenile or young donors would extremely increase the potential for the clinical islet transplantation.

For the porcine pancreas, the histological differences between adult and young animals which substantially hamper a successful islet isolation from the juvenile pancreas have also been pointed out (11, 23, 24). Furthermore, recent investigations show that even in defined breeding lines, significant differences can be proved between individuals of the same age with respect to the isolable islet mass (25).

The preceding statements lead to the conclusion that the specific character of different donor factors requires to be individually taken into consideration when treating a donor pancreas. An user specific isolation procedure contains in particular a modification of the collagenolytic protease mixtures which are used by taking into consideration the above discussed histological results. Available enzymes or enzyme mixtures must allow the user the biggest possible flexibility without overstressing him in the complexity of an individual blending. The availability of a pure class I/class II collagenase mixture, as it can be obtained in form of the NB-1 collagenase of the Nordmark/Serva, complies with this requirement to a wide extent. Depending on the respective donor status, a collagenase concentration which must be individually completed respectively by neutral protease should be adjusted.

The invention will be explained by the following embodiments and examples.

Example 1

The adaptation of the neutral protease activity successfully supports the isolation of islet cells of pigs after a long-term cold storage.

In order to save the short ressources of human organs at a wide extent, preliminary tests are carried out with pigs. Among them, we find in particular the titration of limit concentrations of collagenase and neutral protease which is first evaluated on adult (>24 months) porcine pancreata. Since the NB-1 collagenase is first available only in limited quantity, isolations of porcine islets are carried out with NB-8 collagenases. This being, only charges which are characterized by a minimal content of neutral protease and trypsin as well as by the lowest possible content of clostripain are used. Preliminary tests show here that the digestion time and the quantity of the digestible tissue is clearly correlated with the concentration of neutral protease.

In order to guarantee a constant enzyme concentration for each test series, the distended collagenase quantity will be adapted to the quantity of the tissue used. This is contrary to the propagated Liberase protocol of the Roche company for which a constant enzyme quantity of 500 mg should be used independently of the mass of tissue (26). For three collagenase concentrations which have to be determined preliminarily empirically (for example 4 mg/g organ, 6 mg/g and 8 mg/g), the optimal quantity of neutral protease is iteratively titrated in the range of approx. 0.2-0.6 DMC-U/g organ.

|  | NB-8 collagenase | | |
|---|---|---|---|
| Neutral protease | 4 mg/g | 6 mg/g | 8 mg/g |
| 0,2 DMC-U/g | | | |
| 0,3 DMC-U/g | | | |
| 0,4 DMC-U/g | | | |
| 0,5 DMC-U/g | | | |
| 0,6 DMC-U/g | | | |

The digestion duration, the ratio of tissue inserted to digested tissue, the islet yield, the purity and the mean islet size are considered to be relevant isolation parameters. The most effective mixture is tested on 6 organs. The islets which are then isolated are subject to a quality control which considers the functionality and viability of the islets as well in vitro by statical glucose stimulation and membrane integrity colorations as in vivo by means of the diabetic nude mouse bioassays. The presumably best combination of NB-I collagenase and neutral protease should be confirmed by tests with NB-1 collagenase on 8 organs as well.

Due to empirically collected experience, it is possible to adapt these iterative optimization tests to juvenile (approx. 6 months old) donor pigs and to repeat them in a reduced extent for promising enzyme combinations.

The same is also valid for the optimization tests with NB-1 collagenase for the human isolation procedure. By practice-orientated consideration of age-related donor factors, two age classes are formed for pancreas donors which reflect the experience obtained until now: <25 years, 25 years. The above mentioned titration scheme for neutral protease should be adapted for human pancreata and carried out for two preliminarily empirically to determined collagenase concentrations (for example 4 mg/g and 5 mg/organ).

| Donor: | NB-1 collagenase | | | |
|---|---|---|---|---|
|  | <25 years | | >25 years | |
| Neutral protease | 4 mg/g | 5 mg/g | 4 mg/g | 5 mg/g |
| 0,5 DMC-U/g | | | | |
| 1,0 DMC-U/g | | | | |
| 1,5 DMC-U/g | | | | |
| 2,0 DMC-U/g | | | | |
| 2,5 DMC-U/g | | | | |

The presumably most effective combination of NB-1 collagenase and neutral protease is tested for each age class on 6 organs and the isolated cells are subject to a quality control in vitro and in vivo (s. below).

An individual dosage is possible due to the use of neutral protease with purified or partially purified collagenase with a defined low content of neutral protease. A preparation of the enzyme mixture takes place with respect to units instead of mass, since the specific activity is very unequal.

The adaptation of the neutral protease activity successfully supports the isolation of islet cells of pigs after a long time cold storage.

Background:

The enzymatic dissociation of pancreatic tissue through collagenase constitutes a decisive step in the process of the isolation of islet cells. The variability of the pancreatic collagen for different types led to the production of specific enzyme mixtures. However, the enzyme mixtures available at the moment do not offer the possibility to dose individual components by means of individual donor variables, for example the cold ischemia time. We suppose that the individual adaptation of the neutral protease activity could be used as a critical factor of the enzymatic pancreas digestion in order to facilitate the successful release of islet cells. In order to prove this hypothesis, pancreata of pigs have been subject to a cold long-term storage (6.5 hours) before the dissociation took place by means of NB-8 collagenase of Serva which is characterized by a minimal quantity of neutral protease.

Method:

After sampling, pancreata of no longer used breeding animals have been intraductally distended with NB-8 collagenase, dissolved in a cold UW solution. The definitive collagenolytic activity was 4 FZ-U/g pancreatic tissue. After preliminary experiences, neutral protease (Serva) has been adapted to 0.6 or 0.9 DMC-U/g or 0.14 DMC-U/g for freshly prepared (n=5) or stored pancreata (n=5). Islet cells have been isolated by modified digestion-filtration and purified on a Cobe 2991 by using Ficoll sodium diatrizoate. The quality control comprised the trypane blue exclusion sample and the statical glucose incubation (2.8 to 20 mM glucose). Moreover, the mitochondrial activity has been evaluated by means of the formazan production and at 490 nm determined by using a tetrazolium compound (MTS) and expressed as arbitrary units (AU) per mg proteine.

Results:

The total digestion time for long-term stored pancreata has been considerably shortened compared to freshly prepared pancreata (48±3 compared to 63±3, P<0.05). No differences have been stated with respect to the pancreas weight and the quantity of digested tissue. After the purification of islet cells which have been isolated with 0.14 or 0.9 DMC-U/g, no significant differences have been stated with respect to the definitive purity (>95%), to the islet partition (>95%) and the recuperation of islet cell tissue (73±9 compared to 72±16). After long-term storage, the islet cell yield was slightly lower compared to freshly isolated preparations (146,000±43,000 compared to 212,000±52,000 IEQ, NS) but not significantly lower. The quality control resulted in an outstanding islet cell viability (99.9±1 compared to 99.4±0.3%, NS), a preserved intracellular insulin content (1720±96 compared to 1760±280 µU/IEQ, NS) as well as a comparable glucose stimulation index (1.7±0.2 compared to 1.5±0.1, NS) after the digestion with 0.14 or 0.6 or 0.9 DMC-U/g. The mitochondrial activity was not different between the islet cells isolated after the long-term storage (0.85±0.06 AU/mg) and freshly prepared cells (0.90±0.11 AU/mg).

Conclusions:

This study demonstrates with a model of long-term stored porcine pancreata that the individual dosage of single components of an enzyme mixture is useful according to the individual donor variables in order to facilitate the release of islet cells. The individual adaptation of the neutral protease activity could also be useful for the consideration of the warm ischemia, of the donor age and of the fatty or fibrous degeneration of pancreatic tissue.

Example II

Determination of the optimal relation of neutral protease to collagenase for the isolation of islets of Langerhans Aim:

Determination of the optimal relation of neutral protease/collagenase (NPCR) in the enzyme mixture which is used for the isolation of islets of Langerhans. Serva collagenase mixtures with different NPCR are compared with each other and with Liberase and type V collagenase as controls for a rat model.

Background:

Liberase is at present the universally used enzyme mixture for the isolation of human islets. Its development was a definitive improvement compared with crude collagenases in so far as it was purified, free from endotoxine and showed little its variability from charge to charge for the enzymatic activity.

However, since the results of the islet transplantation are proceeding quickly, it is necessary to further improve the configuration and standardization of the enzyme mixtures which are available on the market. There is for example no standardization of the released Liberase charges with respect to activities per gram of the product of the different enzymatic components. Thus, there is a considerable variability from charge to charge for the collagenase activity, the activity of the neutral protease and for the NPCR, as this is shown in the analysis certificates of the producer. For this reason, the optimal NPCR for the islet isolation is not known. It is also conceivable that an adapted NPCR could be necessary for each pancreas, according to its structure, the age of the donor, the ischemia time. A new enzyme which is available on the market is Serva collagenase, packed in separate phials with the neutral protease. This allows a specific blending of the two components in order to achieve a predetermined ratio instead of carrying out the isolation with a ratio which has been preliminarily fixed by the producer and which varies from charge to charge. With the rat model, it is to determine which is the optimal NPCR for the islet isolation.

Methods:

Seven groups of Lewis rats will be used as islet donors. 18 rats will be in each group. The groups will be determined as follows:

Group 1:
Islet isolation with pure Serva collagenase, without neutral protease (NPCR=0% w/w)

Group 2:
Islet isolation with Serva collagenase, with a NPCR of 3% w/w

Group 3:
Islet isolation with Serva collagenase, with a NPCR of 6% w/w

Group 4:
Islet isolation with Serva collagenase, with a NPCR of 12% w/w

Group 5:
Islet isolation with Serva collagenase, with a NPCR of 24% w/w

Group 6:
Islet isolation takes place with Liberase RI.

Group 7:
Islet isolation takes place with type V collagenase (Sigma).

Example IIA

The role of neutral protease during the islet isolation, evaluated with a new enzyme preparation Aim:

Several enzyme preparations are available for the islet isolation. One of them is a highly purified product with separate components (collagenase and neutral protease) which allows the adaptation of the neutral protease concentration for the islet isolation. For this study, we evaluate the role of neutral protease during the islet isolation.

Method:

Seven groups of Sprague-Daley rats (18 rats per group) have been formed for the standardized islet isolation according to the enzyme type. We charged for group I type XI collagenase by 2 mg/ml (Sigma Chemical, for group II Liberase by 0.6 mg/ml (Roche) and in the groups III to VII NB1 collagenase 0.6 mg/ml (Serva Electrophorese). Pure NB 1 collagenase has been charged for group III. For the groups IV, V, VI and VII, a concentration of 7.5, 15, 22 and/or 30 µg/ml neutral protease (NP) has been added. The results have been evaluated with respect to the islet yields, apoptosis (cell death detection ELISA, Roche and Tunel coloration), of cytokines (IL-1β, IL-6, TNFα, IFNγ) secretions (Quantikine M, R&D system), insulin secretion (statical incubation) and islet morphology (histology and immuno-histology).

Results:

The endotoxine content of the enzyme solution was for the groups I and II 173+22 and 120+11 EU/ml. For the groups III to VII, it increased gradually, according to the NP concentration, from 0.4 to 58 EU/ml (p<0.05). The islet equivalent (IE) yields per rat were 1367+522 and 1755+110 for group I and/or II. For the groups III to VII, the IE yields per rat followed a Gaussian distribution according to the NP concentration with a higher yield for the group V, 1712+245 and a lower for the group III (597+277) and the group VII (905+297) (p=0.05). For the groups III to VII, the islet morphology was influenced by the NP concentration with a decreasing number of captured islets and an increasing number of fragmented islets as the NP content increased. The increase of the NP concentration was related to a progressive deterioration of the α cell ring of the islet which was comparable for the group VII with the deterioration which has been observed for the groups I and II. The release of cytokines (IL-1β, IL-6, TNFα, IFNγ) was lower in the groups III to VII compared with the groups I and II, however it was not influenced by the NP concentration, the islet cell necrosis and apoptosis were statistically significantly lower in the groups III to VII compared with the groups I and II, however they were not influenced by the NP concentration. The mean stimulation indizes of the insulin secretion were 2.96 for the group I, 5, 17 for the group II and they were between 5.25 and 5.43 for the groups III to VII.

Conclusion:

Neutral protease is a decisive additive to collagenase for the islet isolation with respect to islet yields. The Serva collagenase with an appropriate concentration of neutral protease can be compared with the Liberase with respect to the islet yields and function. However, it is related with a lower release of islet cell cytokines and to apoptosis, what results in an improved cell morphology.

Example III

Successful long-term preservation of pancreas by means of the two-layer method for the subsequent isolation of porcine islet cells Background:

The special sensitivity of porcine islet cells prevented the successful isolation from pancreata after cold long-term storage. For the successful isolation of human islet cells, the oxygen accumulation in pancreatic tissue has been recently developed by means of the two-layer method (TLM) during the cold storage. Up to now, no data are available about the long-term preservation of porcine pancreata by means of TLM. Therefore, the aim of this study was to examine the efficiency of the TLM for the successful isolation of islet cells of porcine pancreata which have been submitted to a TLM preservation for 6.5 hours (n=5) compared to freshly prepared pancreata (n=5).

Method:

Immediately after sampling, pancreata of no longer used breeding animals have been intraductally distended with collagenase (Serva), diluted in a cold UW solution with a concentration of 4 mg per g pancreatic tissue. Islet cells have been isolated by modified digestion-filtration and purified on a Cobe 2991 by using Ficoll sodium diatrizoate. The quality control comprised the trypan blue exclusion sample and the statical glucose incubation (2.8 to 20 mM glucose). Furthermore, the mitochondrial activity has been evaluated by means of the formazan production and determined at 490 nm by using a tetrazolium compound (MTS) and expressed as arbitrary units (AU) per mg protein.

Results:

After purification, no significant differences could be stated between freshly prepared pancreata and TLM preserved pancreata with respect to the definitive purity (>95%), the yield (2440±580 compared to 1800±250 IEQ/g), the viability (99.4±0.3 compared to 100.0±0.0 IEQ/g) and the glucose stimulation index (1.73±0.19 compared to 1.48±0.14, NS) of islet cells. The intracellular insulin content was increased after the TLM preservation compared to the fresh preparation (2250±110 compared to 1760±280 μU/IEQ, NS). Compared to the freshly isolated islet cells, the mitochondrial activity has been maintained by the TLM during the long-term storage (0.96±0.15 compared to 1.01±0.17 AU/mg, NS).

Conclusions:

This study demonstrates the efficiency of the TLM for the long-term preservation of porcine pancreata before the successful isolation of islet cells.

Example IV

Comprises the storage of the tissue (porcine pancreas) with the two-layer method on perfluoro hydrocarbons, tissue dissociation through individual adding of neutral protease.

Perfluoro hydrocarbons has a high oxygen combining capacity. Thus, the stored tissue is better supplied with oxygen so that the metabolism can be better maintained and the tissue better withstands the storage of a few hours. For the isolation of cells, the digesting enzyme solution has been added either before the storage (TLM preloaded) or after the storage (TLM postloaded). Again the variation possibility of the quantity of the added neutral protease is important (for a constant collagenase concentration of 4 PZ-U/g organ): preload lower quantity (0.1 DMC-U/g organ since a longer digesting time is given by the storage) and postload higher quantity (0.9 DMC-U/g organ).

This being, optimization of the cell isolation results by variation of the neutral protease and storage method.

Data in the Table I:

These are the detailed data concerning yield of islet cell equivalents, viability, integrity of the islet cells.

The data show that the results which can be achieved with respect to yield of islet cell equivalents, viability, integrity of the islet cells or islet cell aggregates are comparably good independently of the storage (2=TLM-preloaded (4 PZ-U; 0.1 DMC-U); 4=UW-preloaded (4 PZ-U; 0.1 DMC-U); 3=TLM-postloaded (4 PZ-U; 0.9 DMC-U) or non storage (6=unstored (4-PZ-U; 0.9 DMC-U)) when the quantity of neutral protease is adapted correspondingly.

TABLE I

| Exp. | Isolation result before purification | | | | | | after purification | | | | | |
|---|---|---|---|---|---|---|---|---|---|---|---|---|
| Grp. | IEQ Pre | SEM | n | IEQ/IN Pre | SEM | n | IEQ Post | SEM | n | IEQ/IN Post | SEM | n |
| 6 | 382467 | 69415 | 6 | 0.81 | 0.08 | 6 | 388877 | 100179 | 6 | 0.90 | 0.09 | 6 |
| 3 | 245500 | 51272 | 6 | 0.73 | 0.15 | 6 | 238550 | 37398 | 6 | 0.69 | 0.10 | 6 |
| 2 | 309357 | 32394 | 7 | 0.84 | 0.08 | 7 | 210429 | 22852 | 7 | 0.68 | 0.06 | 7 |
| 4 | 192228 | 22697 | 7 | 0.72 | 0.07 | 7 | 108957 | 34669 | 7 | 0.60 | 0.06 | 7 |

TABLE I-continued

| Significance: | ns | | | ns | | | ns | | | 3:2 | |

| Exp. Grp. | IEQ Rec. (%) | SEM | n | OD/10³IE | SEM | n | Si | SEM | n | mU/10³IE | SEM |
|---|---|---|---|---|---|---|---|---|---|---|---|
| 6 | 97.5 | 15.6 | 6 | 0.701 | 0.048 | 6 | 2.76 | 0.42 | 6 | 678 | 13 |
| 3 | 104.6 | 18.7 | 6 | 0.760 | 0.043 | 6 | 1.86 | 0.29 | 6 | 648 | 8 |
| 2 | 69.1 | 4.6 | 7 | 0.792 | 0.030 | 7 | 1.47 | 0.15 | 7 | 682 | 3 |
| 4 | 83.6 | 8.2 | 7 | 0.803 | 0.034 | 7 | 1.56 | 0.15 | 7 | 1060 | 13 |
| Significance: | ns | | | 6:2 | | | ns | | | | |

6 = without storage (4 PZ-U, 0, 9 DWC-U)
3 = TLM storage, enzyme addition after storage (4 PZ-U, 0, 1 DMC-U)
2 = TLM storage, enzyme addition before storage (4 PZ-U, 0, 1 DMC-U)
4 = Storage in UW buffer, enzyme addition before storage (4 PZ-U, 0, 1 DMC-U)
IEQ/IN = Fragmentation index
OD = Mitochondrial activity
MU = Insulin content

The invention claimed is:

1. A method for production of a two component product consisting of a neutral protease (NP) and a collagenase, the method comprising (i) determining a mixing ratio of NP to collagenase needed for isolation of islets of Langerhans from a pancreatic tissue, and (ii) mixing a separately prepared A component with a separately prepared B component in the mixing ratio directly before combining the product with the pancreatic tissue to be dissociated, wherein the A component is a completely purified neutral protease (NP) from *Clostridium histolyticum* which is not contained in a collagenase enzyme preparation and which is not produced by a recombinant production, and the B component is a purified or partially purified collagenase.

2. The method according to claim 1, wherein the mixing ratio of component A to component B is 3% (w/w), 6% (w/w), 12% (w/w), or 24% (w/w).

* * * * *